United States Patent [19]

Lerot et al.

[11] Patent Number: 5,089,454
[45] Date of Patent: Feb. 18, 1992

[54] CATALYTIC COMPOSITION FOR HYDROGENATION OF CHLOROFLUOROALKENES

[75] Inventors: Luc Lerot; Jean-Louis Costa, both of Brussels; Vincent Wilmet, Louvain-La-Neuve; Joseph Pirotton, Brussels, all of Belgium

[73] Assignee: Solvay & Cie (Société Anonyme), Brussels, Belgium

[21] Appl. No.: 347,926

[22] Filed: May 5, 1989

[30] Foreign Application Priority Data

May 24, 1988 [FR] France ............... 88 06991

[51] Int. Cl.$^5$ .............. B01J 21/10; B01J 27/10; B01J 27/12; B01J 27/138
[52] U.S. Cl. .................... 502/226; 570/157
[58] Field of Search ........... 502/328, 330, 229, 230, 502/226, 224; 570/157

[56] References Cited

U.S. PATENT DOCUMENTS

| | | | |
|---|---|---|---|
| 2,207,868 | 7/1940 | Martin | 502/330 |
| 2,476,920 | 7/1949 | Segura | 260/449.6 |
| 3,505,417 | 4/1970 | Gardner | 260/653.5 |
| 3,846,281 | 11/1974 | Mertzweiller | 208/139 |
| 3,876,557 | 4/1975 | Bland | 502/328 |
| 4,289,710 | 9/1981 | Kaiser | 502/328 |
| 4,621,149 | 11/1986 | Fukuoka et al. | 560/24 |

FOREIGN PATENT DOCUMENTS

| | | |
|---|---|---|
| 0053657 | 6/1982 | European Pat. Off. . |
| 0257561 | 3/1988 | European Pat. Off. . |
| 2583039 | 6/1986 | France . |
| 58-167556 | 10/1983 | Japan .......... 502/230 |

Primary Examiner—W. J. Shine
Attorney, Agent, or Firm—Spencer & Frank

[57] ABSTRACT

The invention relates to catalytic compositions for the hydrogenation of chlorofluoroalkenes to fluoroalkenes, comprising a porous carrier impregnated with metal of group VIII of the Periodic Table of the elements and with one or more compounds chosen from the salts of an alkali metal or alkaline-earth metal.

The invention also relates to a process for obtaining these catalytic compositions and a process of hydrogenation by means of these catalytic compositions.

7 Claims, No Drawings

CATALYTIC COMPOSITION FOR HYDROGENATION OF CHLOROFLUOROALKENES

The invention relates to catalytic compositions permitting the hydrogenation of chlorofluoroalkenes to fluoroalkenes and more particularly the hydrogenation of chlorotrifluoroethylene to trifluoroethylene, as well as a process for obtaining such catalytic compositions.

The hydrogenation of chlorotrifluoroethylene to trifluoroethylene involving catalysts comprising, on the one hand, a carrier such as alumina and, on the other hand, a metal of group VIII of the Periodic Table of the elements is a reaction which has been known for a long time (U.S. Pat. No. 2,697,124).

These catalysts have undergone many improvements and have led to processes such as described particularly in European Patent 53,657, which concerns a process for hydrogenation of chlorotrifluoroethylene to trifluoroethylene involving catalysts consisting of a metal of the platinum group deposited onto a particular carrier such as a mixed salt of sodium magnesium fluoride or of potassium magnesium fluoride; this catalyst can be reactivated at an elevated temperature such as 400° to 600° C., with a gas containing oxygen.

However, all these catalytic synthesis processes known hitherto have a relatively low catalytic activity and are accompanied by secondary reactions and/or a rapid catalyst deactivation, and this compromises the efficacy of these processes.

The invention, on the other hand, concerns a catalytic synthesis process which no longer exhibits these disadvantages. Catalytic compositions have, in fact, been found, which enable chlorofluoroalkenes to be hydrogenated with a selectivity and a degree of conversion, that is to say a yield, which have never been achieved industrially, and which furthermore offer the advantage of being stable and of being deactivated much more slowly than the known catalytic compositions and of being capable of regeneration at moderate temperature.

For this purpose, the invention concerns catalytic compositions for the hydrogenation of chlorofluoroalkenes to fluoroalkenes comprising a porous carrier onto which are deposited a metal of group VIII of the Periodic Table of the elements and one or more compounds chosen from the salts of an alkali metal or alkaline-earth metal.

The salts of an alkali metal or alkaline-earth metal which are employed are organic or inorganic salts of these metals. The organic salts employed are generally carboxylates, alcoholates or acetylacetonates whose alkyl chain usually contains from 1 to 10 carbon atoms. The inorganic salts employed are generally halides, hydroxides or nitrates and, more particularly, the halides or the hydroxides of an alkali metal or alkaline-earth metal, such as sodium, potassium, caesium, lithium, barium, calcium or rubidium chlorides, fluorides or hydroxides. Sodium, potassium, caesium or barium chlorides, fluorides or hydroxides are advantageously chosen, such as caesium chloride, potassium chloride, barium chloride, caesium fluoride and caesium hydroxide. Caesium chloride, potassium chloride or barium chloride are preferably employed.

The catalytic compositions may comprise one or more compounds chosen from the salts of an alkali metal or alkaline-earth metal. Good results have been obtained with one or two of these compounds. A binary composition chosen from caesium, potassium or barium chlorides is preferably employed. Compositions simultaneously containing barium chloride and caesium chloride are particularly preferred.

The catalytic compositions according to the invention comprise from 1 to 25% by weight of alkali metal or alkaline-earth metal relative to the total weight of the catalytic composition. They preferably comprise from 5 to 20% by weight of alkali metal or alkaline-earth metal relative to the total weight of the catalytic composition. When a number of compounds are employed, the proportions between each compound may vary within wide limits. Good results have been obtained with barium chloride and caesium chloride used in ratios of barium and caesium of between 2:1 and 1:2.

Palladium, platinum, rhodium, ruthenium, cobalt or nickel and, preferably, palladium or platinum are usually employed as a metal of group VIII of the Periodic Table of the elements.

The catalytic compositions according to the invention usually comprise from 0.05 to 10% by weight of metal of group VIII relative to the total weight of the catalytic composition, and preferably from 0.1 to 5%. Good results have been obtained when the rate ratio between the alkali metal or alkaline-earth metal and the metal group VIII is between 0.1 and 15 and more particularly when this ratio is between 2 and 6.

A porous carrier such as those generally used in the previous catalytic compositions employed in a hydrogenation reaction of this type is usually employed as a carrier for the catalytic compositions of the invention. A carrier based on carbon, active charcoal, alumina, alkali magnesium fluoride, silica, fluorinated alumina, titanium oxide, magnesium oxide, zirconium oxide, zinc fluoride or on the hydroxides of these metals is generally employed. Good results have been obtained with alumina, silica and the mixture of alumina and silica, as well as with titanium oxide, zirconium oxide and magnesium oxide and/or hydroxide.

The pore volume of the carrier may vary within wide limits; it is generally between 0.1 and 5 cm$^3$/g and usually between 0.4 and 2 cm$^3$/g.

The specific surface area of the carrier may vary within wide limits; it is generally between 5 and 1,000 m$^2$/g, and usually between 10 and 550 m$^2$/g.

The catalytic compositions may be obtained according to various processes.

For this purpose, the catalytic compositions may be obtained by impregnation of the carrier with solutions containing the metal of group VIII of the Periodic Table of the elements and one or more compounds chosen from the salts of an alkali metal or alkaline-earth metal. This impregnation may be carried out by any method, such as especially by the so-called "pore volume" technique (so-called "dry" impregnation) or by the "excess volume" technique (so-called "wet" route impregnation); these methods are described in the book by Charles N. Satterfield "Heterogeneous catalysis in practice", 1980, McGraw-Hill Book Company, New York, in particular on pages 82 and 83.

The metal of group VIII of the Periodic Table of the elements is usually introduced into the compositions of the invention in the form of a salt of this metal. To do this, a chloride or an ammoniacal complex of the metal of group VIII is generally used.

The impregnating solutions may be aqueous or organic; an aqueous or alcoholic solution is preferably used.

The impregnation may be carried out initially with a solution containing the metal of group VIII of the Periodic Table of the elements, or initially with a solution containing one or more compounds chosen from the salts of an alkali metal or alkali-earth metal, or simultaneously with both solutions.

A method for obtaining catalytic compositions of the invention with which good results have been obtained consists in impregnating the carrier during a first stage with an aqueous solution containing one or more compounds chosen from the salts of an alkali metal or alkaline-earth metal and then, after drying, during a second stage with an aqueous solution containing a salt of the metal of group VIII of the Periodic Table of the elements, a water-soluble salt such as, especially, a chloride or an ammoniacal complex. Good results have been obtained with a chloride. These impregnations are generally performed at ambient temperature with an aqueous solution containing the desired quantities of salts of an alkali metal or alkaline-earth metal, and then of a salt of the metal of group VIII. The drying between the two impregnations takes place at 350° C. for 2 hours. This impregnated carrier is then dried at 120° C. and is then introduced into the actual hydrogenation reactor. The catalytic composition thus obtained may be used as such or may be reduced beforehand, either with hydrogen or with a mixture of hydrogen with an inert gas such as helium. The temperature at which this reduction is carried out is generally between 100° and 500° C.; good results have been obtained with a reduction temperature of between 150° and 250° C. The pressure at which this reduction is carried out is generally between 1 and 5 bars.

The catalytic compositions according to the invention may be used in any hydrogenation process, such as especially the processes carried out with a catalyst arranged as a stationary bed or a fluidized bed.

The catalytic compositions according to the invention can be used for the synthesis of any fluoroalkene from the corresponding chlorofluoroalkene. Good results have been obtained in the case of the synthesis of trifluoroethylene from chlorotrifluoroethylene.

More particularly, the invention relates to a process for the hydrogenation of chlorotrifluoroethylene to trifluoroethylene, in which the reaction is catalysed by a catalytic composition comprising a porous carrier onto which a metal of group VIII of the Periodic Table of the elements and one or more compounds chosen from the salts of an alkali metal or an alkaline-earth metal have been deposited.

The temperature at which the hydrogenation reaction takes place is usually between 80° and 600° C. This temperature is preferably between 120° and 400° C. Good results have been obtained with a reaction temperature situated in the region of 200°-300° C.

The pressure at which the hydrogenation reaction is carried out is not critical as such. The operation is usually carried out with pressures of between 1 and 10 bars and preferably with pressures of between 2 and 5 bars.

The volume ratio between the chlorotrifluoroethylene and the hydrogen employed is generally between 0.05 and 4. This ratio is preferably between 0.1 and 2.5. Good results have been obtained with a ratio situated in the region of 1.

The mean contact time is generally between 2 and 16 s; this time is usually between 3 and 10 s. Good results have been obtained with a contact time of between 4 and 8 s.

The catalytic compositions according to the invention make it possible to obtain a selectivity higher than 90% and most of the time higher than 95%; the production of byproducts is low, most of the time below 5%. The degree of conversion of chlorotrifluoroethylene is high, higher than 40%.

After the use of the catalytic compositions of the invention it is observed that the regeneration of the catalytic composition is easy and can be carried out in situ in the hydrogenation reactor. A regeneration method which has given good results consists in regenerating the catalytic compositions under a stream of air and then under a stream of hydrogen. The performance of the catalytic compositions after the regeneration is very closely related to that observed with fresh catalytic compositions. This regeneration of the catalytic compositions is generally performed at a moderate temperature, that is to say at temperatures of between 100° and 400° C. and preferably 200° and 300° C.

The invention is more amply illustrated by the following examples.

EXAMPLE 1:

a) Preparation of the Catalytic Composition 10 g of silica which has the following characteristics are introduced into a 40-cm$^3$ cylindrical impregnation ampoule:

B.E.T. specific surface area of 250 m$^2$/g pore volume approximately 0.8 cm$^3$/g.

The ampoule is heated under vacuum (3 mm Hg) for 2 hours at 350° C. in a cylindrical oven in order to degas the silica.

After cooling under vacuum the silica is impregnated at ambient temperature under vacuum in an 8.8-cm$^3$ volume of an aqueous solution containing 1 g of caesium chloride and 1.25 g of barium chloride; the volume of this solution corresponds to the pore volume of the carrier increased by 10%.

The materials are allowed to stand for 1 hour under a static vacuum and then overnight at atmospheric pressure at ambient temperature.

The silica thus impregnated is then dried at 350° C. under vacuum (1 to 6×10$^2$ Pa) for 2 hours.

This silica is then impregnated at ambient temperature under vacuum (1 to 6×10$^2$ Pa) in an 8.8-cm$^3$ volume of a solution containing 0.17 g of palladium chloride in water acidified with 4% by volume of concentrated hydrochloric acid; the volume of this solution corresponds to the pore volume of the carrier increased by 10%.

The materials are left to stand for 1 hour under vacuum and then overnight at atmospheric pressure at ambient temperature.

They are then dried for 3 hours at 120° C. at atmospheric pressure.

The catalytic composition thus obtained comprises 0.8% by weight of palladium, 6.6% by weight of barium and 6.4% by weight of caesium relative to the total weight of the catalytic composition.

2 cm$^3$ of this catalytic composition are introduced into a hydrogenation reactor consisting of a stainless steel metal tube 520 mm in length and with an internal diameter of 7.7 mm; the catalytic composition is then aged for 2 hours at 500° C. under 3 bars by means of a mixture of hydrogen and helium in a volume ratio of 1/9 at a flow rate of 40 cm$^3$/min.

b) Hydrogenation of Chlorotrifluoroethylene

The reactor is fed at a rate of 0.05 mole per hour of chlorotrifluoroethylene and 0.05 mole per hour of hydrogen at 240° C. and 3 bars. The main contact time is estimated at 5.3 s.

After 4 hours' operation, the degree of conversion of chlorotrifluoroethylene to trifluoroethylene is 60%; the selectivity for trifluoroethylene is higher than 96%.

After 100 hours' operation, the degree of conversion is 55% with a selectivity of 94%.

c) Regeneration of the Catalytic Composition

After use, the catalytic composition is regenerated in situ in the hydrogenation reactor.

To do this, a stream of air is introduced into the reactor for 2 hours, followed by a stream of hydrogen for 2 hours at 240° C.

The performance of the catalytic composition after this regeneration is comparable to that obtained with a fresh catalytic composition.

EXAMPLES 2, 3 AND 4:

Hydrogenation of Chlorotrifluoroethylene

The reactor, consisting of a stainless steel metal tube 520 mm in length and with an inner diameter of 7.7 mm, is charged with 2 cm$^3$ of a catalytic composition such as described in Example 1.

The catalytic composition is reduced at 240° C. for 2 hours using a flow rate of 0.01 mole of hydrogen per hour diluted 10-fold with helium at 3 bars.

This reactor is fed with chlorotrifluoroethylene and with hydrogen at 240° C. at 3 bars with the quantities shown in Table 1 below. The mean contact time is estimated at 5.3 s.

The results after 4 hours' operation (the degree of conversion of chlorotrifluoroethylene to trifluoroethylene and the selectivity) are also shown in Table 1.

drogen at 240° C. at 3 bars. The mean contact time is estimated at 3 s.

The degree of conversion of chlorotrifluoroethylene is 86% after 1 h of operation, 80% after 24 h and 77% after 70 h.

The selectivity for trifluoroethylene is 95%.

EXAMPLE 6

The reactor described in Example 1 is charged with a catalytic composition comprising a porous carrier consisting of silica which has a specific surface area of 250 m$^2$/g and a pore volume of 1.7 cm$^3$/g and is impregnated with 16% by weight of CsCl and with 4.5% by weight of PdCl$_2$ according to the method of preparation described in Example 1.

The catalytic composition is reduced at 500° C. for 2 hours using a flow rate of 0.01 mole of hydrogen per hour, diluted 10-fold with helium at 1 bar.

The reactor is fed at a rate of 0.05 mole per hour of chlorotrifluoroethylene and 0.05 mole per hour of hydrogen at 240° C. at 1 bar. The mean contact time is estimated at 1.7 s.

After 16 hours' operation, the degree of conversion of chlorotrifluoroethylene is 54%.

The selectivity for trifluoroethylene is 95%.

EXAMPLE 7

A catalytic composition is prepared by following the procedure described in Example 1a.

The carrier consists of silica such as that described in Example 1.

6.2% by weight of barium, 5.2% by weight of caesium and 0.83% by weight of palladium are used, calculated relative to the total weight of the reduced catalytic composition; these metals were used in the form of chloride.

The catalytic composition is reduced outside the reactor at 150° C. at 3 bars using a mixture of hydrogen and helium in a volume ratio of 1/9 at a flow rate of 40 cm$^3$/min.

The catalytic composition is then introduced into a

TABLE 1

| EXAMPLES | REACTOR FEED IN MOLE PER HOUR OF | | DEGREE OF CONVERSION OF CHLOROTRIFLUORO- ETHYLENE TO TRIFLUORO- ETHYLENE VOLUME % | SELECTIVITY-FOR TRIFLUOROETHYLENE VOLUME % |
|---|---|---|---|---|
| | CHLOROTRIFLUORO- ETHYLENE | HYDROGEN | | |
| 2 | 0.05 | 0.05 | 54 | 95 |
| 3 | 0.015 | 0.08 | 80 | 93 |
| 4 | 0.050 | 0.025 | 46 | 97 |

EXAMPLE 5:

The reactor described in Example 1 is charged with a catalytic composition comprising a porous carrier consisting of alumina with a specific surface area of 350 m$^2$/g and with a pore volume of 1.7 cm$^3$/g and impregnated with 19% by weight of BaCl$_2$ (13.6% of barium relative to the total weight of the catalytic composition) and with 4.3% by weight of PdCl$_2$ (2.8% by weight of palladium relative to the total weight of the catalytic composition) according to the method of preparation described in Example 1.

The catalytic composition is reduced at 500° C. for 2 hours using a flow rate of 0.01 mole of hydrogen per hour, diluted 10-fold with helium at 3 bars.

The reactor is fed at a rate of 0.05 mole per hour of chlorotrifluoroethylene and 0.05 mole per hour of hyhydrogenation reactor identical with that described in Example 1.

The reactor is fed at a rate of 0.05 mole per hour of chlorotrifluoroethylene and 0.05 mole per hour of hydrogen at 280° C. at 3 bars. The mean contact time is estimated at 4.9 s.

After 4 hours' operation, the degree of conversion of chlorotrifluoroethylene to trifluoroethylene is 60%; the selectivity for trifluoroethylene is 94%.

After 16 hours' operation, the degree of conversion is 66% and the selectivity is 94%.

EXAMPLE 8

By following the procedure described in Example 1, a catalytic composition is prepared, comprising a porous carrier consisting of silica which has a specific surface area of 250 m$^2$/g and a pore volume of 1.7 cm$^3$/g, and which is impregnated with 13.5% by weight of CsCl (10.6% by weight of caesium relative to a total weight of the reduced catalytic composition) and with 1.4% by weight of PdCl$_2$ (0.85% by weight of palladium relative to the total weight of the reduced catalytic composition).

The catalytic composition is reduced at 150° C. outside the reactor for 2 hours using a flow rate of 0.01 mole of hydrogen per hour, diluted 10-fold with helium at 1 bar.

This catalytic composition is introduced into a reactor identical with that described in Example 1.

The reactor is fed at a rate of 0.05 mole per hour of chlorotrifluoroethylene and 0.05 mole per hour of hydrogen at 240° C. at 3 bars. The mean contact time is estimated at 5.3 s.

After 4 hours' operation, the degree of conversion of chlorotrifluoroethylene is 41%.

The selectivity for trifluoroethylene is 95%.

After 16 hours' operation, the degree of conversion of chlorotrifluoroethylene is 45% and the selectivity is 96%.

EXAMPLE 9 a) Preparation of the Catalytic Composition 10 g of magnesium oxide which has the following characteristics are introduced into a 40-cm$^3$ cylindrical impregnation ampoule:

B.E.T. specific surface area of 23 m$^2$/g pore volume approximately 0.3 cm$^3$/g, having previously soaked up 2 cm$^3$ of water and been left at rest for 16 hours and then dried under vacuum (100 to 200 Pa).

The ampoule is heated under vacuum (3 mm Hg) for 2 hours at 350° C. in a cylindrical oven in order to degas the magnesium oxide.

After cooling under vacuum, the magnesium oxide is impregnated at ambient temperature under vacuum in a 2-cm$^3$ volume of an aqueous solution containing 0.52 g of caesium chloride.

The materials are allowed to stand for 1 hour under static vacuum and then overnight at atmospheric pressure at ambient temperature.

Thus impregnated, the magnesium oxide is then dried at 90° C. under vacuum (1 to 6×10$^2$ Pa) for 2 hours.

This magnesium oxide is then impregnated at ambient temperature under vacuum (1 to 6×10$^2$ Pa) in a 2-cm$^3$ volume of a solution containing 0.08 g of palladium chloride in water acidified with 10% by volume of concentrated hydrochloric acid.

The materials are allowed to stand for 1 hour under vacuum and then overnight at atmospheric pressure at ambient temperature.

They are then dried for 2 hours at 90° C. under vacuum (1 to 6×10$^2$ Pa).

The catalytic composition thus obtained comprises 0.45% by weight of palladium and 4% by weight of caesium relative to the total weight of the catalytic composition.

2 cm$^3$ of this catalytic composition are introduced into a hydrogenation reactor consisting of a stainless steel metal tube 520 mm in length and with an internal diameter of 7.7 mm; the catalytic composition is then aged for 2 hours at 500° C. at 3 bars using a mixture of hydrogen and helium in a volume ratio of 1/9 at a flow rate of 40 cm$^3$/min.

b) Hydrogenation of Chlorotrifluoroethylene

The reactor is fed at a rate of 0.05 mole per hour of chlorotrifluoroethylene and 0.05 mole per hour of hydrogen at 240° C. at 3 bars. The mean contact time is estimated at 5.3 s.

After 10 hours' operation, the degree of conversion of chlorotrifluoroethylene to trifluoroethylene is 64%; the selectivity for trifluoroethylene is higher than 94%.

After 70 hours' operation, the degree of conversion and the selectivity are unchanged.

We claim:

1. A catalytic composition for the hydrogenation of a chlorofluoroalkene to fluoroalkene comprising a magnesium oxide porous carrier, a palladium or platinum metal, and at least two compounds chosen from among potassium, caesium, or barium chlorides or fluorides.

2. The catalytic composition according to claim 1, including from about 1 to 25% by weight of potassium, caesium or barium.

3. The catalytic composition according to claim 1, including from about 0.05 to 10% by weight of palladium or platinum.

4. The catalytic composition set forth in claim 1, wherein the chlorofluoroalkene is chlorotrifluoroethylene.

5. A catalytic composition for hydrogenation of a chlorofluoroalkene to fluoroalkene, comprising a magnesium oxide porous carrier, a metal selected from the group consisting of palladium and platinum, and caesium chloride.

6. A catalytic composition for hydrogenation of a chlorofluoroalkene to fluoroalkene, comprising a magnesium oxide porous carrier, a metal selected from the group consisting of palladium and platinum, and caesium fluoride.

7. A catalytic composition for hydrogenation of a chlorofluoroalkene to fluoroalkene, comprising a magnesium oxide porous carrier, a metal selected from the group consisting of palladium and platinum, and potassium chloride or potassium fluoride.

* * * * *